(12) United States Patent
Couturier et al.

(10) Patent No.: US 6,569,967 B1
(45) Date of Patent: May 27, 2003

(54) ALKOXYAMINES DERIVED FROM β-PHOSPHOROUS NITROXIDES

(75) Inventors: Jean-Luc Couturier, Lyons (FR); Christiane Henriet-Bernard, Hofheim-Lorsbach (DE); Christophe Le Mercier, Marseilles (FR); Paul Tordo, Marseilles (FR); Jean-Francois Lutz, Montpellier (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/913,940

(22) PCT Filed: Feb. 10, 2000

(86) PCT No.: PCT/FR00/00335
§ 371 (c)(1),
(2), (4) Date: Mar. 19, 2002

(87) PCT Pub. No.: WO00/49027
PCT Pub. Date: Aug. 24, 2000

(30) Foreign Application Priority Data

Feb. 18, 1999 (FR) .............................................. 99 01998

(51) Int. Cl.$^7$ ................ C08F 4/00; C07F 9/40
(52) U.S. Cl. ........... 526/193; 526/328; 526/346; 558/175; 560/170; 564/15; 564/16
(58) Field of Search ................ 526/193, 328, 526/346; 558/175; 560/170; 564/15, 16

(56) References Cited

U.S. PATENT DOCUMENTS 3,767,708 A * 10/1973 Smith et al. ............ 260/563 R
4,755,614 A * 7/1988 Corbet ..................... 558/134
5,077,329 A 12/1991 Pastor

OTHER PUBLICATIONS

Hawker C J et al.: "Initiating Systems For Nitroxide–Mediated "Living" Free Radical Polymerizations: Synthesis ANd Evaluation"Macromolecules, vol. 29, No. 16, Jul. 29, 1996, pp. 5245–5254, XP000596748, ISSN: 0024–9297, cited in the application, the whole document.
Shatzmiller S.: "Synthesen von alpha–Aminophosphonsauren aus N–Ethoxy–iminium–Salzen, II" Justus Liebigs Annalen Der Chemie., No. 9, 1993—Sep. 1993, pp. 955–958, XP002115861, Verlag Chemie Gmbh. Weinheim., DE, ISSN: 0075–4617, p. 956, formulas 5–17, 24, 25.
Shatzmiller S.: "Synthesis of alpha–Amino Phosphonic Acids via Oxoiminium Salts" Justus Liebigs Annalen Der Chemie., No. 2, 1991—Feb. 1991, pp. 161–164, XP002115862, Verlag Chemie Gmbh. Weinheim., DE, ISSN: 0075–4617, formulas 9a et 9b.
Le Mercier C et al.: "Characteristics of phosphonylated nitroxides and alkoxyamines used in controlled/"living" radical polymerizations", Polym. Prepr. (Am. Chem. Soc., Div. Polym. Chem.) (ACPPAY, 00323934); 1999; vol. 40 (2); pp. 313–314, XP000909196, CNRS et Universities, d'Aix–Marseille; Laboratoire Structure et Reactivite des Especes Paramagnetiques; Marseille; 13397; Fr. (FR), in particular composites of formulas 6–8.
Benoit D. et al.: "Development of a Universal Alkoxyamine for "Living" Free Radical Polymerizations" J. Am. Chem. Soc. (JACSAT, 00027863); 1999; vol. 121 (16); pp. 3904–3920, XP002115863, IBM Almaden Research Center; NSF Center for Polymeric Interfaces and Macromolecular Assemblies; San Jose; 95120–6099; CA; USA (US), in particular pp. 3908 and 3917, composite 27.
Marsal P et al.: "Thermal stability of O–H and O–alkyl bonds in N–alkoxyamines. A density functional theory approach", J. Phys. Chem. A (JPCAFH, 10895639); 1999; vol. 103 (15); pp. 2899–2905, XP002115864, CNRS et Universities d'Aix–Marseille I et III; Laboratoire de Chimie Theorique UMR 6517; Marseille; 13397; Fr. (FR) *in Universities d'Aix–Marseille I et III; Laboratoire de Chimie Theorique UMR 6517; Marseille; 13397; Fr. (FR) *in particular figure 1 and table 3*.
International Search Report for Application No. PCT/FR00/00335.

* cited by examiner

*Primary Examiner*—Fred Teskin
(74) *Attorney, Agent, or Firm*—Millen, White, Zelano & Branigan, P.C.

(57) ABSTRACT

The invention concerns alkoxyamines derived from β-phosphorous nitroxides corresponding to formula (I). Said compounds can be used as (co)polymerization initiators of at least a monomer polymerizable by radical polymerization.

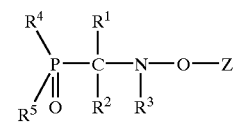

18 Claims, 1 Drawing Sheet

ALKOXYAMINES DERIVED FROM β-PHOSPHOROUS NITROXIDES

Figure 1:
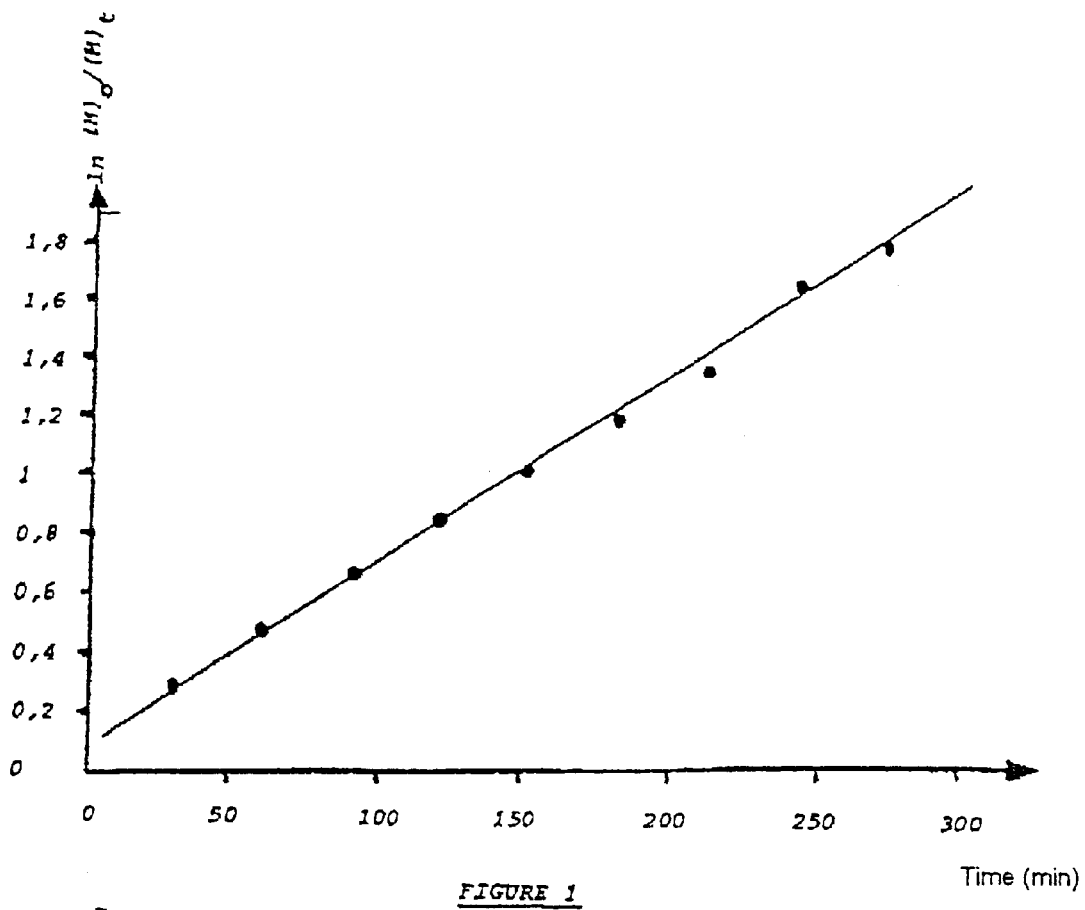

The present invention relates to α,β,β-trisubstituted hydroxylamines, referred to hereinbelow as alkoxyamines, obtained from β-phosphorous nitroxides, which may be used in particular as free-radical polymerization initiators. The use of alkoxyamines such as those derived from 2,2,6,6-tetramethylpiperidyl N-oxide (TEMPO) in the preparation of macromolecules has given rise to many publications.

Thus, Hawker C. J. et al. (Macromolecules 1996, 29, pages 5245–5254) showed that the use of alkoxyamines derived from TEMPO such as (2',2',6',6'-tetramethyl-1'-piperidyloxy)methylbenzene as free-radical polymerization initiators of styrene make it possible to control the polymerization and to gain access to well-defined polymers with low polydispersity indices, and they have found that the polymerization rates are substantially equivalent to the rates obtained when conventional initiators such as AIBN or benzoylperoxide are used in the presence of TEMPO.

It has now been found that the use of alkoxyamines derived from β-phosphorous nitroxides as polymerization or copolymerization initiators for at least one monomer which may undergo a free-radical polymerization affords excellent control of the polydispersity while at the same time ensuring a good rate of polymerization or copolymerization.

One subject of the invention is thus alkoxyamines of formula:

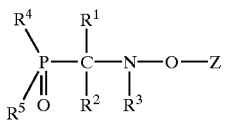

in which $R^1$ and $R^2$, which may be identical or different, represent a hydrogen atom, a linear or branched alkyl radical containing a number of carbon atoms ranging from 1 to 10, an aryl radical, an aralkyl radical containing a number of carbon atoms ranging from 1 to 10, or $R^1$ and $R^2$ are linked together so as to form a ring including the carbon atom bearing said $R^1$ and $R^2$, said ring containing a number of carbon atoms, including the carbon bearing the radicals $R^1$ and $R^2$, ranging from 3 to 8; $R^3$ represents a linear or branched, saturated or unsaturated hydrocarbon-based radical which may comprise at least one ring, said radical containing a number of carbon atoms ranging from 1 to 30; $R^4$ and $R^5$, which may be identical or different, represent a linear or branched alkyl radical, a cycloalkyl, aryl, alkoxy, aryloxy, aralkyloxy, perfluoroalkyl, aralkyl or thioalkyl radical containing a number of carbon atoms ranging from 1 to 20, or $R^4$ and $R^5$ are linked together so as to form a ring including the phosphorus atom, said heterocycle containing a number of carbon atoms ranging from 2 to 6 and possibly also containing one or more oxygen or sulfur atoms;

Z is a cycloalkyl radical containing 3–12 carbon atoms or a residue of formula:

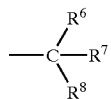

in which $R^6$, $R^7$ and $R^8$, which may be identical or different, represent a hydrogen atom, a linear or branched alkyl radical containing a number of carbon atoms ranging from 1 to 10, a phenyl radical, a benzyl radical, a cyano radical or a cycloalkyl radical containing from 3 to 12 carbon atoms; a radical —$(CH_2)n$-C(O)O$R^9$ in which $R^9$ represents a linear or branched alkyl containing a number of carbon atoms ranging from 1 to 6 and n=0 to 6.

Among the compounds of formula (I), the ones that are most particularly preferred are those in which $R^1$=H, $R^2$=$R^3$=$(CH_3)_3$C—, $R^4$=$R^5$=$CH_3CH_2$O—, Z=$C_6H_5CH_2$—, $(CH_3)_2$C (CN)—($R^6$=$R^7$=$CH_3$—, $R^8$=NC—), $CH_3$OC(O)C$(CH_3)_2$—, ($R^6$=$R^7$=$CH_3$—, $R^8$=—$(CH_2)nC(O)$ O$R^9$ with n=0 and $R^9$=—$CH_3$); $CH_3$OC(O)CH(CH$_3$)—($R^6$=H, $R^7$=$CH_3$—, $R^8$=—$(CH_2)_n$C(O)O$R^9$ with n=0 and $R^9$=—$CH_3$); $C_6F_{13}$—, $C_6H_5$CH(CH$_3$)—, $C_6H_5$C(CH$_3$)$_2$—, $C_6H_{12}$—, $CH_3(CH_2)_5$—.

The alkoxyamines of formula (I) may be prepared according to methods known in the literature. The most common method involves the coupling of a carbon-based radical with a nitroxide radical. The carbon-based radical Z. may generated by various methods described in the literature: decomposition of an azo compound, abstraction of a hydrogen atom from a suitable substrate, addition of a radical to an olefin. The radical Z. may also be generated from an organometallic compound, for instance an organomagnesium reagent Z—MgX as described by Hawker C. J. et al. in Macromolecules 1996, 29, 5245–5254 or from a halo derivative Z—X in the presence of an organometallic system such as CuCl/bipyridine according to a reaction of ATRA (Atom Transfer Radical Addition) type as described by Dorota Greszta et al. in Macromolecules 1996, 29, 7661–7670.

Among all these methods, the one which will preferably be used to prepare the compounds of formula (I) is the method involving the ATRA reaction.

This method consists in transferring an atom or a group of atoms onto another molecule in the presence of an organometallic catalytic system such as CuBr/bipyridine and in a solvent medium.

The procedure generally used consists in dissolving the organometallic complex such as CuBr/bipyridine in an organic solvent, preferably an aromatic solvent such as benzene or toluene, and then in introducing into the solution the compound ZX and the β-phosphorous nitroxide.

The reaction mixture is then stirred at a temperature of between 20° C. and 70° C. for a period at least equal to 48 hours, or even longer.

Next, the precipitate is filtered off, rinsed with a solvent such as ether and then washed with an aqueous 5% by weight $CuSO_4$ solution and finally with water.

After drying over $MgSO_4$, the solvents are evaporated off under reduced pressure.

The alkoxyamines of formula (I) according to the present invention may be used for the polymerization and copolymerization of any monomer containing a carbon-carbon double bond which is capable of undergoing free-radical polymerization. The polymerization or copolymerization is carried out under the usual conditions known to those skilled in the art taking the monomer(s) into consideration. The monomers under consideration may be a vinylaromatic monomer (styreree or substituted styrenes), a diene, an acrylic monomer such as methyl acrylate or butyl acrylate or a methacrylic monomer. The monomer may also be vinyl chloride, vinylidene difluoride or acrylonitrile.

The alkoxyamines (1) may advantageously be introduced into the polymerization or copolymerization medium at contents ranging from 0.005% to 5% by weight relative to the monomer(s) used.

The examples which follow illustrate the invention.
The β-phosphorous nitroxide or formula:

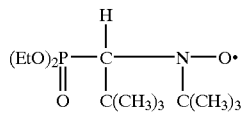

will be used in the examples below and will be denoted as DEPN.

It was obtained by oxidation of diethyl 2,2-dimethyl-1-(1,1-dimethylethylamino)propyl phosphonate using meta-chloroperbenzoic acid according to a protocol described in international patent application The compounds obtained were characterized by elemental analysis and by $^1H$, $^{13}C$, $^{31}P$ and $^{19}F$ NMR.

The NMR spectra were acquired on a Bruker AC 100 machine ($^1H$, 100 MHz; $^{31}P$, 40.53 MHz; $^{19}F$, 94.22 MHz; $^{13}C$, 25.18 MHz). The $^{13}C$ and $^{31}P$ NMR spectra are acquired with $^1H$ decoupling.

The chemical shifts δ are given in ppm relative to tetramethylsilane (internal reference) for the proton and carbon, relative to 85% $H_3PO_4$ (external reference) for phosphorus and relative to trifluoroacetic acid for fluorine.

EXAMPLE 1

Synthesis of N-tert-butyl-N-1-diethylphosphono-2,2-dimethylpropyl-O-1-phenylethylhydroxyl-amine (1)

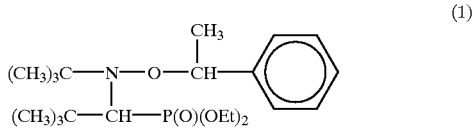

0.57 g of $CuBr_4$ (4 mmol) and 1.25 g of 2,2'-bipyridine (8 mmol) are introducedd into a 100 ml Schlenk tube purged with argon. 0.74 g of (1-bromo-ethyl)benzene (4 mmol) and 0.68 g of 86% DEPN (2 mmol) dissolved in 9 ml of anhydrous toluene are added. The mixture is left to react with stirring for 48 hours at room temperature. The reaction mixture is filtered through Celite. The filtrate is washed with aqueous 5% copper sulfate solution and then with water. The organic phase is dried over magnesium sulfate and the solvent is then evaporated off. The product is purified by chromatography on a column of silica, using a 6/4 pentane/ether eluent. 0.75 g of compound (1) (yield=95%) is obtained in the form of two diastereoisomers in 64/36 proportions determined on the $^{31}P$ spectrum of the crude mixture by integration of the signals at 23.14 and 24.36 ppm (I/II=64/36).

The analytical results are given below:

Isomer I:

$^{31}P$ NMR (CDCl$_3$): δ23.14

$^1H$ NMR (CDCl$_3$): δ0.88 (t, $J_{H-H}$=7.2 Hz, 3H); 1.21–1.27 (m, 21H); 1.55 (d, $J_{H-H}$=6.6 Hz, 3H) (s, 9H); 3.40 (d, $J_{H-P}$=26 Hz, 1H); 3.18–3.40 and 3.70–4.05 (m, 4H); 5.22 (q, $J_{H-H}$=6.6 Hz, 1H); 7.24–7.47 (m,5H).

$^{13}C$ NMR (CDCl$_3$): δ16.23 (2d, $J_{C-P}$=7 Hz, CH$_3$CH$_2$), 21.18 (s, CH$_3$CH), 28.19 (s, CH$_3$—C—CH), 30.63 (d, $J_{C-P}$=7 Hz, CH$_3$—CN), 35.33 (d, $J_{C-P}$=6 Hz, C—CH—P), 58.58 (d, $J_{C-P}$=7.5 Hz, C=CH$_3$), 61.4 (d, $J_{C-P}$=7 Hz, CH$_2$—O), 70.06 (d, $J_{C-P}$=138.5 Hz, CH—P), 78.36 (s, CH—O), 127.33 (s,CH ar), 127.81 (s, CH ar), 127.88 (s, CH ar), 143.31 (s, C ar).

Microanalysis ($C_{21}H_{37}NO_4P$): % calculated C, 63.12; H, 9.59; N, 3.51. % found C, 63.01; H, 9.60; N 3.42.

Isomer II:

$^{31}P$ NMR, (CDCl$_3$) δ24.36. 1H NMR (CDCl$_3$): δ0.82 (s,9H); 1.22 (s,9H); 1.29 (t, $J_{H-H}$=7.0 Hz, 3H); 1.32 (t, $J_{H-H}$=7.0 Hz, 3H); 1.58 (d, $J_{H-H}$=6.7 Hz, 3H); 3.32 (d, $J_{H-P}$=26.2 Hz, 1H); 3.9–4.2 and 4.3–4.4 (m, 4H); 4.97 (q, $J_{H-H}$=6.8 Hz, 1H); 7.17–7.3 (m, 5H).

$^{13}C$ NMR (CDCl$_3$): δ16.24 (d, $J_{C-P}$=7.1 Hz, CH$_3$CH$_2$), 16.71 (d, $J_{C-P}$=5.2 Hz, CH$_3$CH$_2$), 24.00 (s,CH$_3$CH), 28.50 (s, CH$_3$—C—CH), 30.12 (d, $J_{C-P}$=5.7 Hz, CH$_3$—C—N), 35.37 (d, $J_{C-P}$=5.8 Hz, C—CH—P), 58.80 (d,$J_{C-P}$=7.4 Hz, CH$_2$—O), 61.10 (s, C—N), 61.56 (d, $J_{C-P}$=6 Hz, CH$_2$—O), 69.84 (d, $J_{C-P}$=138.4 Hz, CH—P), 85.23 (s, CH—O), 126.96 (s, CH ar), 127.08 (s, CH ar), 127.95 (s, CH ar), 145.36 (s, C ar).

Microanalysis ($C_{21}H_{37}NO_4P$): % calculated C, 63.12; H, 9.59; N, 3.51. % found C, 63.05; H, 9.51; N, 3.50.

EXAMPLE 2

Synthesis of N-tert-butyl-N-1-diethylphosphono-2,2-dimethylpropyl-O-benzyl-hydroxylamine (2)

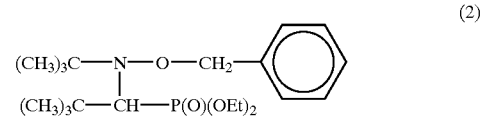

The procedure is the same as for Example 1. The reagents used are: benzyl bromide (1.03. g, 6 mmol), CuBr (0.86 g, 6 mmol), 2,2'-bipyridine (1.87 g, 12 mmol), 72% DEPN (1.23 g, 3 mmol), benzene (16 ml). The product is purified by chromatography on a column of silica (7/3 pentane/ethyl acetate eluent). 0.46 g of compound (2) (yield=40%) is obtained in the form of a white solid with a melting point equal to 68–70° C.

The analytical results are given below:

Microanalysis ($C_{20}H_{36}NO_4P$):

% calculated: C, 62.32; H, 9.41; N, 3.63

% found: C, 62.52; H, 9.27; N, 3.18.

$^{31}P$ NMR (CDCl$_3$): δ23.38

$^1H$ NMR (CDCl$_3$): δ1.01 (t, $J_{H-H}$=7 Hz, 3H), 1.17 (s, 9H), 1.20 (s, 9H), 1.23 (t, $J_{H-H}$=7 Hz, 3H), 3.26 (d, $J_{H-P}$=24.3 Hz, 1H), 3.45–3.8 and 3.85–4.2 (m, 4H), 4.56 (d, $J_{H-H}$=9.3 Hz, 1H), 5.21 (d, $J_{H-H}$=9.5 Hz, 1H), 7.27.5 (m, 5H)

$^{13}C$ NMR (CDCl$_3$): δ16.18 (d, $J_{C-P}$=7.1 Hz, CH$_3$CH$_2$), 16.31 (d, $J_{C-P}$=5.8 Hz, CH$_3$CH$_2$), 27.74 (s, CH$_3$—C—CH), 30.10 (d, $J_{C-P}$=6.34 Hz, CH$_3$—C—N), 35.26 (d, $J_{C-P}$=5.4 Hz, C—CH—P), 58.72 (d, $J_{C-P}$=7.3 Hz, CH$_2$), 61.56 (d, $J_{C-P}$=7.0 Hz, CH$_2$—O), 61.97 (s, C—N), 69.64 (d, $J_{C-P}$=140 Hz, C$_{H-P}$), 77.79 (s, CH$_2$—O) 127.65 (s, CH ar), 127.95 (s, CH ar); 129.56 (s, CH ar), 136.79 (s, C ar).

EXAMPLE 3

Synthesis of N-tert-butyl-N-1-diethylphosphono-2, 2-dimethylpropyl-O-1-cyano-1-methylethylhydroxylamine (3)

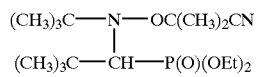
(3)

The procedure is the same as for Example 1. The reagents used are: 2-bromo-2-methylpropionitrile (0.89 g, 6 mmol), CuBr (0.86 g, 6 mmol), 2,2'-bipyridine (1.87 g, 12 mmol), 72% DEPN (1.23 g, 3 mmol), benzene (16 ml). The product is purified by chromatography on a column of silica (5/5 pentane/ethyl acetate eluent). 0.77 g of compound (3) (yield=73%) is obtained.

The 2-bromo-2-methylpropionitrile is prepared by brominating isobutyronitrile with N-bromosuccinimide in refluxing $CCl_4$.

The analytical results are given below:

$^{31}$P NMR ($CDCl_3$): δ23.04

$^1$H NMR ($CDCl_3$): δ1.25–1.37: m, 1.72 (s, 3H), 1.89 (s, 3H), 3.38 (d, $J_{H-P}$=24.3 Hz, 1H), 3.8 and 4.4 (m, 4H).

$^{13}$C NMR ($CDCl_3$) δ16.25 (d, $J_{C-P}$=6.6 Hz, $CH_3CH_2$), 16.68 (d, $J_{C-P}$=5.4 Hz, $CH_3CH_2$), (s, $CH_3$—C—CH), 28.86 (s, $CH_3$—C—O), 29.07 (s, $CH_3$—C—O), 30.50 (d, $J_{C-P}$=5.5 Hz, $CH_3$), 36.16 (d, $J_{C-P}$=5.5 Hz, C—CH—P), 59.20 (d, $J_{C-P}$=7.3 Hz, $CH_2$), 61.61 (d, $J_{C-P}$=5.9 Hz, $CH_2$), (s, C—N), 69.84 (d, $J_{C-P}$=138.8 Hz, CH—P), 77.78 (s, C—CN), 121.21 (s, CN).

EXAMPLE 4

Synthesis of N-tert-butyl-N-1-diethylphosphono-2, 2-dimethylpropyl-O-1-methoxycarbonylethylhydroxylamine (4)

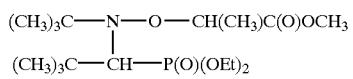
(4)

The procedure is the same as for Example 1. The reagents used are: methyl 2-bromopropionate (1 g, 6 mmol), CuBr (0.86 g, 6 mmol), 2,2'-bipyridine (1.87 g, 12 mmol), 86% DEPN (1.08 g, 3 mmol), benzene (16 ml). The product is purified by chromatography on a column of silica (5/5 pentane/ethyl acetate eluent). 1.07 g of compound (4) are obtained in the form of two diastereoisomers in 56/44 proportions (yield=93%).

Diastereoisomeric ratio in 56/44 proportions determined on the $^{31}$P spectrum of the crude mixture by integration of the signals at 23.55 and 22.96 ppm (I/II=56/44).

Isomer I:

$^{31}$P NMR ($CDCl_3$): δ23.55.

$^1$H NMR ($CDCl_3$): δ1.10 (s, 9H); 1.16 (s, 9H); 1.30 (t, $J_{H-H}$=7 Hz, 6H); 1.50 (d, $J_{H-P}$=7 Hz, 3H); 3.28 (d, $J_{H-P}$=25.3 Hz, 1H); 3.70 (s, 3H); 3.9–4.3 (m, 4H); 4.60 (q 1H).

$^{13}$C NMR ($CDCl_3$): δ16.18 (d, $J_{C-P}$=6 Hz, $CH_3CH_2$), 16.48 (d, $J_{C-P}$=6 Hz, $CH_3CH_2$), 19.09 (s, $CH_3CH$), 27.83 (s, $CH_3$—C—CH), 29.57 (d, $J_{C-P}$=6 Hz, $CH$—C—N), 35.53 (d, $J_{C-P}$=5 Hz, C—CH—P), 51.34 (s, O—$CH_3$), 58.73 (d, $J_{C-P}$=7.4 Hz, $CH_2$), 61.59 (s, C—N), 61.77 (d, $J_{C-P}$=6.6 Hz, $CH_2$), 69.62 (d, $J_{C-P}$=139.4 Hz, CH—P), 82.38 (s, CH—O), 174.33 (s, C=O).

Microanalysis ($C_{17}H_{36}NO_5P$): % calculated C, 53.51; H, 9.52; N, 3.67. % found C, 53.50; H, 9.49; N, 3.55.

Isomer II:

$^{31}$P NMR ($CDCl_3$): δ22.96.

$^1$H NMR ($CDCl_3$): δ1.13 (s, 9H); 1.16 (s, 9H); 1.27 and 1.29 (2t, $J_{H-H}$=7 Hz, 6H); 1.47 (d, $J_{H-H}$=7 Hz, 3H); 3.36 (d, $J_{H-P}$=26.4 Hz, 1H); 3.70 (s, 3H); 3.85–4.3 (m, 4H); 4.65 (q, 1H).

$^{13}$C NMR ($CDCl_3$) δ16.32 (d, $J_{C-P}$=6 Hz, $CH_3CH_2$) 16.66 (d, $J_{C-P}$=6 Hz, $CH_3CH$ ), 17.99 (s, $CH_3CH$), 28.09 (s, $CH_3$—C—CH), 30.35 (d, $J_{C-P}$=6 Hz, $CH_3$—C—N), 37.47 (d, $J_{C-P}$=5 Hz, C—CH—P), 51.54 (s, O—$CH_3$), 59.02 (d, $J_{C-P}$=7.7 Hz, $CH_2$), 61.51 (s, C—N), 61.97 (d, $J_{C-P}$=6 Hz, $CH_2$), 69.39 (d, $J_{C-P}$=139.6 Hz, CH—P), 77.10 (s, CH—O), 173.23 (s, C=O).

Microanalysis ($C_{17}H_{36}NO_5P$): % calculated C, 53.51; H, 9.52; N, 3.67. % found C, 53.39; H, 9.34; N, 3.50.

EXAMPLE 5

Synthesis of N-tert-butyl-N-1-diethylphosphono-2, 2-dimethylpropyl-O-1-methyl-1-methoxycarbonylethylhydroxylamine (5)

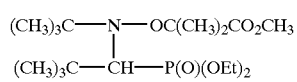
(5)

The procedure is the same as for Example 1. The reagents used are: methyl 2-bromo-2-methylpropionate (1.09 g, 6 mmol), CuBr (0.86 g, 6 mmol), 2,2'-bipyridine (1.87 g, 12 mmol), 86% DEPN (1.08 g, 3 mmol), benzene (16 ml). The product is purified by chromatography on a column of silica (5/5 pentane/ethyl acetate eluent). 0.47 g of compound (5) (yield=43%) is obtained.

Methyl 2-bromo-2-methylpropionate is prepared by reacting methanol with 2-bromo-2-methylpropionyl bromide.

$^{31}$P NMR ($CDCl_3$): δ24.46.

$^1$H NMR ($CDCl_3$): δ1.10 (s, 9H); 1.17 (s, 9H); 1.28 (m, 6H); 1.57 and 1.63 (2s, 6H); 3.24 (d, $J_{H-P}$=26 Hz, 1H); 3.67 (s, 3H); 3.9–4.3 (m, 4H).

$^{13}$C NMR ($CDCl_3$): δ18.75 (d, $J_{C-P}$=6.9 Hz, $CH_3CH_2$), 16.11 (d, $J_{C-P}$=5.9 Hz, $CH_3CH_2$), 22.60 (s, $CH_3$—C—O), 26.79 (s, $CH_3$—C—O), 27.71 (s, $CH_3$—C—CH), 29.39 (d, $J_{C-P}$=5.7 Hz, $CH_3$—C—N), 35.44 (d, $J_{C-P}$=6.6 Hz, C—CH—P), 51.33 (s, O—$CH_3$), 58.11 (d, $J_{C-P}$=7.2 Hz, $CH_2$), 61.29 (d, $J_{C-P}$=7.4 Hz, $CH_2$), 61.68 (s, C—N), 69.67 (d, $J_{C-P}$=136.8 Hz, CH—P), 83.61 (s, CH—O), 175.11 (s, C=O).

EXAMPLE 6

Synthesis of N-tert-butyl-N-1-diethylphosphono-2, 2-dimethylpropyl-O-1-perfluorohexylhydroxylamine (6)

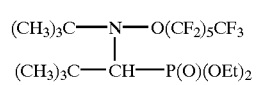
(6)

The procedure is the same as for Example 1, except that the reaction is carried out at 60° C. The reagents used are:

perfluorohexyl iodide (1.34 g, 3 mmol), CuBr (0.43 g, 3 mmol), 2,2'-bipyridine (0.94 g, 6 mmol), 72% DEPN (0.61 g, 1.5 mmol), benzene (10 ml). The product is ourified by chromatography on a columrn of silica (7/3 pentane/ethyl acetate eluent). 0.50 g of the colorless compound (6) is obtained.

The analytical results are given below:

Microanalysis: $C_{19}H_{29}F_{13}NO_4P$:

% calculated: C, 37.20; H, 4.77; N, 2.28

% found: C, 37.18; H, 4.76; N, 2.21

$^{31}P$ NMR $(CDCl_3)$: $\delta 20.65$ $^1H$ NMR $(CDCl_3)$: $\delta 1.19$ (s, 9H), 1.22 (s, 9H) 1.31 (t, 6H), 3.51 (d, $J_{H-P}$=30 Hz, 1H), 4.10 (m, 4H).

$^{19}F$ NMR: $(CDCl_3)$

| δ | 126.61 (m, $C_5F_2$, 2F) |
|---|---|
|   | 123.47–122.66 (m, 6F, $C_2F_2$, $C_3F_2$, $C_4F_2$) |
|   | 81.40 (t, 3F, $J_{FF}$ = 9 Hz, $CF_3$) |
|   | 83.94 (dt, 1F, $J_{FA-FB}$ = 143.3 Hz, $J_{FF}$ = 12.9 Hz, FA) |
|   | 78.66 (dt, 1F, $F_{FA-FB}$ = 152.8 Hz, $J_{FF}$ = 9 Hz, FB) |

$^{13}C$ NMR $(CDCl_3)$

| δ | 16.20 (t, JC-P = 7.4 Hz, $CH_3$—$CH_2$) |
|---|---|
|   | 27.73 (s, $CH_3$—C—CH) |
|   | 30.35 (d, JCP - 3.72 Hz, $CH_3$—C—N) |
|   | 36.33 (d, $J_{C-P}$ = 2.5 Hz, $CH_3$—CH) |
|   | 60.66 (d, JCP = 7.55 Hz, $CH_3$—$CH_2$—O) |
|   | 61.63 (d, JCP = 7.04 Hz, $CH_3$—$CH_2$—O) |
|   | 63.91 (S, C—N) |
|   | 67.46 (d, 137.2 Hz = JCP; CH-P) |
|   | 105.2–121.9 (m, $CF_2$ and $CF_3$) |
|   | 127.8–133.9 (m, $CF_2$) |

EXAMPLE 7

Synthesis of N-tert-butyl-N-1-diethylphosphono-2,2-diethylpropyl-O-1-hexylhydroxylamine (7)

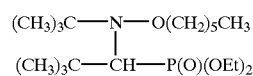
(7)

1.03 g of 94% DEPN (3.3 mmol) and 30 ml of THF predistilled over sodium/benzophenone are introduced into a 100 ml Schlenk tube purged with argon. The solution is cooled to −90° C. and 0.6 ml of a 2.5 M solution of hexyllithium in hexane (1.5 mmol) is added dropwise by syringe via a septum. The reaction mixture is returned slowly to room temperature and is then hydrolyzed with saturated $NH_4Cl$ solution. The aqueous phase is extracted 3 times with ether. The organic phases are combined and dried over magnesium sulfate, and the solvents are then evaporated off. The product is purified by chromatography on a column of silica, using a 75/25 pentane/ethyl acetate eluent. 0.36 g or compound (7) (yield=59%) is obtained.

$^{31}P$ NMR $(CDCl_3)$: $\delta 83.72$ $^1H$ NMR $(CDCl_3)$: $\delta 0.88$ (t, 3H); 1.13 and 1.15 (2s, 18 H) 1.25–1.32 (m, 12H), 1.52–1.55 (m, 2H), 3.21 (d, $J_{H-P}$=24 Hz, 1H), 3.60 (q, 1H), 3.92–4.17 (m, 5H). $^{13}C$ NMR: $(CDCl_3)$: $\delta 14.03$ (s, $CH_3$), 16.29 (d, $J_{C-P}$=6.2 Hz, $CH_3CH_2$), 16.63 (d, $J_{C-P}$=5.8 Hz, $CH_3CH_2$), 22.61 (s, $CH_2$), 25.70 (s, $CH_2$), 27.74 (s, $CH_3$—C), 28.61 (s, $CH_2$), 29.90 (d, $J_{C-P}$=6.5 Hz, $CH_3$—C—N), 31.87 (s, $CH_2$), 35.31 (d, $J_{C-P}$=5.8 Hz, $CH_3$—C—CH), 58.80 (d, $J_{C-P}$=7.3 Hz, $CH_2$), 61.40 (d, $J_{C-P}$=6.51 Hz, $CH_2$—O), 61.60 (C—N), 69.59 (d, $J_{C-P}$=139.8 Hz, CH—P), 76.45 (s, $CH_2$—C).

Microanalysis $(C_{19}H_{42}NO_4P)$: % calculated C, 60.11; H, 11.16; N, 3.69; and % found C, 60.10; H, 11.22; N, 3.62.

EXAMPLE 8

Synthesis of N-tert-butyl-N-1-diethylphosphono-2,2-dimethylpropyl-O-cyclohexylhydroxylamine (8)

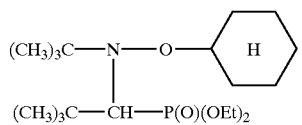
(8)

The procedure is the same as for example 7. The reagents used are: 94% DEPN (1.03 g, 3.3 mmol), cyclohexylmagnesium bromide (0.75 ml of a 2M solution in ether, 1.5 mmol), THF (30 ml). The product is purified by chromatography on a column of silica (75/25 pentane/ether eluent). 0.42 g of compound (8) (yield=75%) is obtained in the form of a white solid.

$^{31}P$ NMR $(CDCl_3)$: $\delta 23.57$ $^1H$ NMR $(CDCl_3)$: $\delta 1.10$ (t, 9H); 1.15 (s, 9H) 1–1.15 (m, 4H), 1.27 and 1.30 (2t, 6H); 1.56–1.8 (m, 4H); 2.05–2.4 (m, 2H); 3.37 (d, $J_{H-P}$=26.8 Hz, 1H); 3.87–4.28 (m, 5H).

$^{13}C$ NMR $(CDCl_3)$: $\delta 16.37$ (d, $J_{C-P}$=9.2 Hz, $CH_3CH_2$), 16.41 (d, $J_{C-P}$=9.9 Hz, $CH_3CH_2$), 24.95 (s, $CH_2$), 25.21 (s, $CH_2$), 26.30 (s, $CH_2$), 28.18 (s, $CH_2$—C), 30.84 (d, $J_{C-P}$=5.85 Hz, $CH_3$—C—N), 31.99 (s, $CH_2$), 32.42 (s, $CH_2$), 35.32 (d, $J_{C-P}$=5.5 Hz, C—CH—P), 58.80 (d, $J_{C-P}$=7.4 Hz, $CH_2$—O), 60.50 (s, C—N), 61.48 (d, $J_{C-P}$=6 Hz, $CH_2$—O), 69.66 (d, $J_{C-P}$=138.8 Hz, CH—P), 79.67 (s, HC—O).

Microanalysis $(C_{19}H_{40}NO_4P)$: % calculated C, 60.43; H, 10.69; N, 3.71; and % found C, 60.4.1; H, 10.75; N, 3.65.

EXAMPLE 9

Use of N-tert-butyl-N-1-diethylphosphono-2,2-dimethylpropyl-O-1-phenylethylhydroxylamine (1) prepared according to Example 1 as an initiator in the polymerization of styrene Reagents:

The styrene was predistilled under reduced pressure.

Polymerization:

Styrene (4.93 g, i.e. 0.047 mol) and compound (1) (0.0952 g, i.e. 2.38×10⁻⁴ mmol) are introduced into a three-necked flask fitted with a gas inlet. The mixture is then degassed by sparging with argon for 20 minutes, after which it is brought to 123° C. in a thermostatically-maintained oil bath. Throughout the reaction, the medium is stirred with a magnetic bar under inert atmosphere. Samples are taken at regular intervals using a degassed syringe.

Analyses:

The number-average molar masses (Mn) and the polydispersity indices (Ip) were measured by steric exclusion chromatography (SEC). The chromatograms were recorded using a Spectra Physics machine fitted with an SP8810 pump, a Shodex RE-61RI differential refractometer and two Pigel mixed D columns (eluent: THF, 30° C.). The calibrations were carried out with samples of standard polystyrene.

The conversion was determined by measuring the solids content on the samples taken.

The theoretical mass targeted for a total conversion is always $Mn_{th}$=19 800 g/mol.

The results are given in Table 1.

TABLE 1

| Time (minutes) | $Mn_{exp}$ (g/mol) | $I_p$ | Conversion (%) | $Mn_{th}$ (g/mol) | $ln[M]_0/[M]_t$ |
|---|---|---|---|---|---|
| 30 | 5049 | 1.33 | 24.2 | 4792 | 0.27 |
| 60 | 7429 | 1.26 | 36.7 | 7266 | 0.45 |
| 90 | 8906 | 1.26 | 47.3 | 9376 | 0.64 |
| 120 | 10515 | 1.24 | 56.8 | 11251 | 0.83 |
| 150 | 12157 | 1.24 | 63.5 | 12578 | 1.00 |
| 180 | 13002 | 1.24 | 69 | 13677 | 1.17 |
| 210 | 13624 | 1.25 | 74.1 | 14677 | 1.35 |
| 240 | 14114 | 1.25 | 80.6 | 15972 | 1.64 |
| 270 | 14200 | 1.24 | 83.1 | 16455 | 1.77 |

Figure 2:
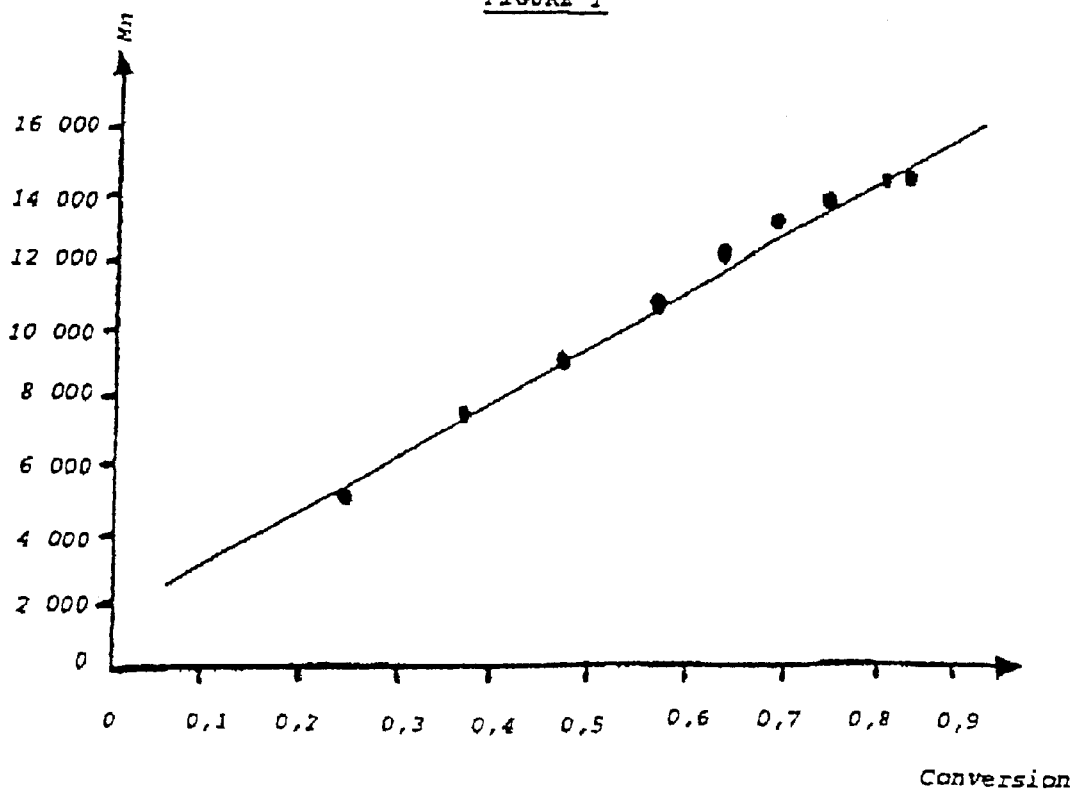

These results make it possible to plot the following two kinetic curves:

in FIG. 1, we have represented the $ln[M]_0/[M]_t$ as a function of time and in FIG. 2 we have represented Mn as a function of the conversion.

The correct alignment of the points and the low polydispersity index ($I_p$) are characteristic of controlled free-radical polymerization.

What is claimed is:

1. A compound of formula:

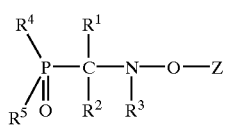

(I)

in which $R^1$ and $R^2$, which may be identical or different, represent a hydrogen atom, a linear or branched alkyl radical containing a number of carbon atoms ranging from 1 to 10, an aryl radical, an aralkyl radical containing a number of carbon atoms ranging from 1 to 10, or $R^1$ and $R^2$ are linked together so as to form a ring including the carbon atom bearing said $R^1$ and $R^2$, said ring having a number of carbon atoms, including the carbon bearing the radicals $R^1$ and $R^2$, ranging from 3 to 8; $R^3$ represents a linear or branched, saturated or unsaturated hydrocarbon-based radical which optionally comprises at least one ring, said radical containing a number of carbon atoms ranging from 1 to 30; $R^4$ and $R^5$, which may be identical or different, represent a linear or branched alkyl radical, a cycloalkyl, aryl, alkoxy, aryloxy, aralkyloxy, perfluoroalkyl, aralkyl or thioalkyl radical containing a number of carbon atoms ranging from 1 to 20, or $R^4$ and $R^5$ are linked together so as to form a ring including the phosphorus atom, said heterocycle containing a number of carbon atoms ranging from 2 to 6 and optionally containing one or more oxygen or sulfur atoms;

Z is a radical $CF_3(CF_2)_5$—, $(CH_3)_2C(CN)$—, or a residue of formula:

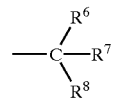

in which $R^6$, $R^7$ and $R^8$, which may be identical or different, represent a hydrogen atom, a cyano radical or a cycloalkyl radical containing a number of carbon atoms ranging from 3 to 12; a radical —$(CH_2)n$-$C(O)OR^9$ in which $R^9$ represents a linear or branched alkyl containing a number of carbon atoms ranging from 1 to 6 and n=0 to 6.

2. The compound as claimed in claim 1, wherein $R^1$=H, $R^2$=$R^3$=$(CH_3)_3C$—, $R^4$=$R^5$=$CH_3CH_2O$— and wherein Z corresponds to one of the residues: $(CH_3)_2C(CN)$—, $CH_3OC(O)C(CH_3)_2$—, $CH_3OC(O)CH(CH_3)$—, $C_6F_{13}$—.

3. A compound according to claim 1, being N-tert-Butyl-N-1-diethylphosphono-2,2-dimethylpropyl-O-1-cyano-1-methylethylhydroxylamine:

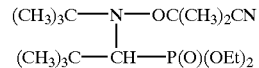

4. A compound according to claim 1, being N-tert-Butyl-N-1-diethylphosphono-2,2-dimethylpropyl-O-1-methyl-1-methoxycarbonylethyl-hydroxylamine:

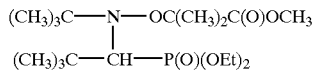

5. A compound according to claim 1, being N-tert-Butyl-N-1-diethylphosphono-2,2-dimethylpropyl-O-1-methoxycarbonylethyl-hydroxylamine:

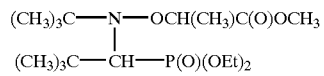

6. A compound according to claim 1, being N-tert-Butyl-N-1-diethylphosphono-2,2-dimethylpropyl-O-1-perfluorohexylhydroxylamine:

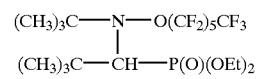

7. In a process comprising polymerizing or copolymerizing at least one monomer in the presence of a free radical initiator, the improvement wherein the initiator comprises at least one compound of the formula:

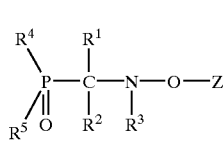

(I)

in which $R^1$ and $R^2$, identical or different, represent a hydrogen atom, a linear or branched alkyl radical containing 1–10 carbon atoms, an aryl radical, an aralkyl radical containing 1–10 carbon atoms, or $R^1$ and $R^2$ are linked together so as to form a ring including the carbon atom bearing said $R^1$ and $R^2$, said ring having 3–8 carbon atoms, including the carbon bearing the radicals $R^1$ and $R^2$, $R^3$ represents a linear or branched, saturated or unsaturated hydrocarbon-based radical optionally comprising at least one ring, said radical containing 1–30 carbon atoms; $R^4$ and $R^5$, identical or different, represent a linear or branched alkyl radical, a cycloalkyl, aryl, alkoxy, aryloxy, aralkyloxy, perfluoroalkyl, aralkyl or thioalkyl radical containing 1–20 carbon atoms, or $R^4$ and $R^5$ are linked together so as to form a ring including the phosphorus atom, said heterocycle containing 2–6 carbon atoms and optionally containing one or more oxygen or sulfur atoms;

Z is a radical $CF_3(CF_2)_5$—, a cycloalkyl radical containing 3–12 carbon atoms or a residue of formula:

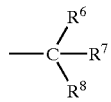

in which $R^6$, $R^7$ and $R^8$, which may be identical or different, represent a hydrogen atom, a linear or branched alkyl radical containing 1–10 carbon atoms, a phenyl radical, a benzyl radical, a cyano radical or a cycloalkyl radical containing 3–12 carbon atoms; a radical —$(CH_2)n$-$C(O)OR^9$ in which $R^9$ represents a linear or branched alkyl containing 1–6 carbon atoms and n=0 to 6.

8. A process as claimed in claim 7, wherein the initiator comprises the compounds of formula (I) in which $R^1$=H, $R^2$=$R^3$=$(CH_3)_3C$—, $R^4$=$R^5$=$CH_3CH_2O$— and in that z corresponds to one of the residues: $C_6H_5CH_2$—, $(CH_3)_2C(CN)$—, $CH_3OC(O)C(CH_3)_2$—, $CH_3OC(O)CH(CH_3)$—, $C_6F_{13}$—, $C_6H_5CH(CH_3)$—, $C_6H_5C(CH_3)_2$—, $C_6H_{12}$—, $CH_3(CH_2)_5$—.

9. A process according to claim 7, wherein the initiator comprises N-tert-butyl-N-1-diethylphosphono-2,2-dimethylpropyl-O-1-phenylethylhydroxylamine:

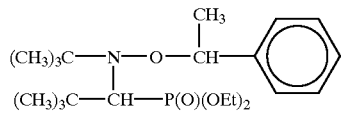

10. A process according to claim 7, wherein the initiator comprises N-tert-butyl-N-1-diethylphosphono-2,2-dimethylpropyl-O-benzylhydroxylamine:

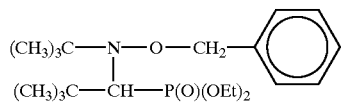

11. A process according to claim 7, wherein the initiator comprises N-tert-butyl-N-1-diethylphosphono-2,2-dimethylpropyl-O-1-cyano-1-methylethylhydroxylamine:

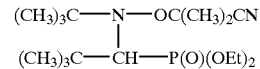

12. A process according to claim 7, wherein the initiator comprises N-tert-butyl-N-1-diethylphosphono-2,2-dimethylpropyl-O-1-methyl-1-methoxycarbonylethylhydroxylamine:

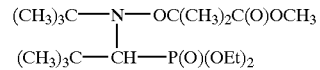

13. A process according to claim 7, wherein the initiator comprises N-tert-butyl-N-1-diethylphosphono-2,2-dimethylpropyl-O-1-methoxycarbonylethylhydroxylamine:

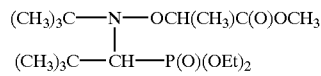

14. A process according to claim 7, wherein the initiator comprises N-tert-butyl-N-1-diethylphosphono-2,2-dimethylpropyl-O-1-perfluorohexylhydroxylamine:

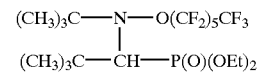

15. A process according to claim 7, wherein the initiator comprises N-tert-butyl-N-1-diethylphosphono-2,2-dimethylpropyl-O-1-hexylhydroxylamine:

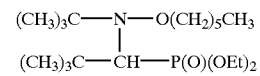

16. A process according to claim 7, wherein the initiator comprises N-tert-butyl-N-1-diethylphosphono-2,2-dimethylpropyl-O-cyclohexylhydroxylamine:

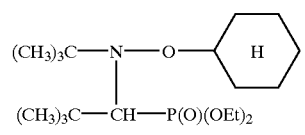

17. A process according to claim 7, wherein the polymerizable monomer comprises styrene, methyl acrylate or butyl acrylate.

18. In a process comprising polymerizing or copolymerizing at least one monomer in the presence of a free radical initiator, the improvement wherein the free radical initiator comprises at least one compound according to claim 1.

* * * * *

UNITED STATES PATENT AND TRADEMARK OFFICE
CERTIFICATE OF CORRECTION

PATENT NO. : 6,569,967 B1   Page 1 of 1
DATED : May 27, 2003
INVENTOR(S) : Jean-Luc Couturier et al.

It is certified that error appears in the above-identified patent and that said Letters Patent is hereby corrected as shown below:

Title page,
Item [75], Inventors, "Lyons," should read -- Lyon --; "Marseilles," should read -- Caluire and Cuire --; "Marseilles," (second occurrence) should read -- Marseille --; and "Montpellier (FR)," should read -- Pittsburgh, PA (US) --

Column 10,
Line 36, reads "methoxycarbonylethyl-hydroxylamine," should read -- methoxycarbonylethylhydroxylamine --

Signed and Sealed this

Twenty-ninth Day of June, 2004

JON W. DUDAS
*Acting Director of the United States Patent and Trademark Office*